United States Patent [19]

Otten et al.

[11] Patent Number: 5,073,286
[45] Date of Patent: Dec. 17, 1991

[54] STABLE ALKYL AND/OR ARYL SILYL ETHER CAPPED POLYETHER SURFACTANTS FOR LIQUID CLEANING AGENTS CONTAINING HYPOHALITE BLEACHES

[75] Inventors: Jay G. Otten, Flat Rock; Edward J. Parker, Riverview; Michael G. Kinnaird, Dearborn, all of Mich.

[73] Assignee: BASF Corporation, Parsippany, N.J.

[21] Appl. No.: 438,312

[22] Filed: Nov. 20, 1989

[51] Int. Cl.$^5$ .......................... C07F 7/02; C07F 7/08; C11D 1/82; C11D 9/36
[52] U.S. Cl. ........................ 252/97; 252/99; 252/174.21; 252/174.22; 252/174.15; 252/94; 556/405; 556/446
[58] Field of Search ............ 252/174.21, 174.22, 252/97, 99, 174.15; 556/405, 446

[56] References Cited

U.S. PATENT DOCUMENTS

| | | | |
|---|---|---|---|
| 2,709,683 | 5/1955 | Sarchet | 252/174.22 |
| 4,005,025 | 1/1977 | Kinstedt | 252/99 |
| 4,005,028 | 1/1977 | Heckert | 252/99 |
| 4,005,117 | 1/1977 | Heckert | 252/548 |
| 4,006,176 | 2/1977 | Heckert | 252/174.15 |
| 4,013,573 | 4/1977 | Leikhim | 252/99 |
| 4,013,574 | 4/1977 | Leikhim | 252/99 |
| 4,136,051 | 1/1979 | Saran | 252/97 |
| 4,280,919 | 7/1981 | Stoeckigt | 252/99 |
| 4,285,840 | 8/1981 | Fricker | 252/174.27 |
| 4,306,987 | 12/1981 | Kaneko | 252/174.22 |
| 4,426,203 | 1/1984 | Abel | 252/174.15 |
| 4,436,642 | 3/1984 | Scott | 252/99 |
| 4,438,014 | 3/1984 | Scott | 252/99 |
| 4,440,662 | 4/1984 | Tsuzuki | 252/174.22 |
| 4,450,091 | 5/1984 | Schmolka | 252/174.22 |
| 4,549,979 | 10/1985 | Chandra | 252/174.15 |
| 4,661,279 | 4/1987 | Parker | 252/174.22 |
| 4,689,082 | 8/1987 | Dexheimer | 252/174.22 |
| 4,774,017 | 9/1988 | Seibert | 252/174.22 |
| 4,824,602 | 4/1989 | Juneja | 252/174.15 |
| 4,913,833 | 4/1990 | Otten | 252/174.22 |

Primary Examiner—Paul Lieberman
Assistant Examiner—Erin M. Higgins

[57] ABSTRACT

An alkyl and/or aryl silyl ether capped polyether surfactant useful in cleaning compositions. The polyether is described in conjunction with automatic dishwashing detergent composition having improved chlorine bleach stability comprising:

(a) an active chlorine containing compound selected from the group consisting of chlorinated trisodium phosphate, chlorinated cyanuric acid and alkali metal salts thereof, 2,3-dichloro-5,5-dimethylhydantoin, hypochlorite bleach and mixtures thereof to yield available chlorine in an amount of from about 0.1 percent to 5 percent;

(b) about 0.1 percent to 5 percent of a chlorine bleach stable nonionic surfactant having the general formula:

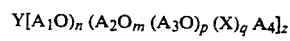

$$Y[A_1O]_n (A_2O)_m (A_3O)_p (X)_q A_4]_z$$

wherein Y is the residue of an organic compound having from 1 to 8, preferably 1 to 4, reactive hydrogens as measured by the Zerevitinov determination method; z is a number from 1 to 8, $A_1$, $A_2$ and $A_3$ are $C_2$ to $C_4$ alkylene groups, tetramethylene, and mixtures thereof; $n+m+p$ are numbers such that the total molecular weight of the uncapped portion of the molecule is from about 500 to 25,000 and the molecular weight of the hydrophile is 5 to 35 weight percent and the molecular weight of the hydrophobe is from 65 to 95 weight percent of the total weight of the molecule; X is a hydrocarbon residue containing 2 to 30 carbon atoms, preferably the residue ($-CR_1R_2CR_3R_4 CR_5R_6-$) where $R_1$, $R_2$, $R_3$, $R_4$, $R_5$ and $R_6$ are H, methyl, and mixtures thereof, q is a number from 0 to 1, $A_4$ is an Si $R'_3$ group wherein $R'$ is a $C_1$ to $C_{30}$ alkyl, a $C_1$ to $C_{30}$ oxyalkyl, a $C_6$ to $C_{30}$ aryl group, and mixtures thereof; and (c) the balance water.

19 Claims, No Drawings

STABLE ALKYL AND/OR ARYL SILYL ETHER CAPPED POLYETHER SURFACTANTS FOR LIQUID CLEANING AGENTS CONTAINING HYPOHALITE BLEACHES

BACKGROUND OF THE INVENTION

1. Field of the Invention

In the art of cleaning compositions for use in cleaning hard surfaces, particularly the art of cleaning tableware and other food-soiled utensils in machine dishwashers, the problem of spotting, filming and defoaming of the machine washload is present. Liquid detergent compositions were introduced to the market and offered ease and convenience of handling. Since their introduction, such detergent compositions have captured upwards of 30 percent of the home market. However, these liquid detergent compositions have suffered certain deficiencies relative to powdered machine dishwashing detergents. Specifically, although they offer ease of manufacture and handling, they have inferior spotting, filming and defoaming characteristics relative to the powdered compositions.

It is believed that these deficiencies are the result of the fact that most detergent compositions contain a chlorine bleach component, such as hypochlorite bleach, and these chlorinating agents degrade conventional defoaming nonionic surfactants such as ethylene oxide/propylene oxide block copolymers and fatty alcohol, fatty acid, fatty amide and alkyl phenol oxyalkylates. As the chlorinating agent attacks the nonionic surfactant, the bleach is depleted and the surfactant is destroyed. Thus, desirable, low spotting, filming and defoaming properties are lost along with the properties of the chlorinating agent.

In the past, liquid automatic dishwashing detergent compositions have been formulated with anionic surfactants such as alkyl diphenyloxide disulfonates, or with no surfactants present at all. The use of anionic surfactants or no surfactants in liquid automatic dishwashing detergent compositions contributes greatly to the spotting, filming and defoaming problems associated with such liquid compositions. Thus, there is a greatly felt need in the industry to formulate a liquid, automatic dishwashing detergent composition which contains nonionic surfactants and which do not break down under attack from chlorinating agents which may be present in the composition.

The present invention relates to the use of alkyl and/or aryl silyl ether capped polyethers as nonionic surfactants in liquid or slurry cleaning formulations which include alkaline hypochlorite bleaching agents. The use of these silyl capped polyethers allows such formulations to retain their cleaning and defoaming properties for longer periods than formulations containing conventional nonionic polyether surfactants.

2. Description of the Related Art

Heckert et al, U.S. Pat. No. 4,005,030 disclosed that the detergent composition containing an anionic detergent and a organosilane is capable of imparting soil release benefits to hard surfaces which are washed therein. The organosilane component of Heckert et al has the formula:

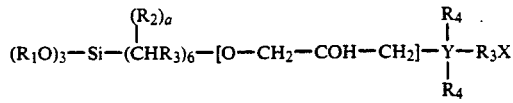

or is a siloxane oligomer thereof wherein $R_1$ is an alkyl group containing 1 to 4 carbon atoms or

where x is 2 to 4, m is 1 to 20, and Z is hydrogen, an alkyl group containing 1 to 3 carbons, or an acyl group containing 1 to 4 carbon atoms; $R_2$ is an alkyl group containing 1 to 12 carbon atoms; a is 0 to 2; $R_3$ is hydrogen or an alkyl group containing 1 to 12 carbon atoms; b is 1 to 3; c is 0 or 1; $R_4$ is an alkyl, aryl or aryl alkyl group containing 1 to 12 carbon atoms, a carboxy-substituted alkyl group containing 1 to 4 carbon atoms,

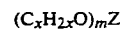

where x, m and Z are as defined above, or oxygen provided only one $R_4$ is oxygen; $R_5$ is an alkyl, aryl or arylalkyl group containing 1 to 12 carbon atoms; X is halide; and Y is nitrogen, sulfur, or phosphorus and the sum of the carbon atoms in $R_2$, $R_3$, and $R_5$ and $R_4$ when $R_4$ is alkyl, aryl, arylalkyl or carboxy-substituted alkyl does not exceed 20 carbon atoms. The present invention is not concerned with siloxanes or polysiloxanes but rather with compositions containing silyl groups. Accordingly the present invention differs from Heckert et al.

Wegst et al, U.S. Pat. No. 3,829,386 disclose an emulsion of a silicone-based foam depressant which is dispersed in low cloud point liquid nonionic surfactants. The surfactants are stable over a wide temperature and concentration range and can be easily incorporated into solid alkaline dishwashing and detergent compositions. There is no mention in Wegst et al of the capping of which is useful in the present invention. Further, it is not contemplated to use the surfactant from dispersant emulsions of Wegst in a liquid detergent composition. There is no recognition of chlorine stability and accordingly the present invention differs from Wegst et al.

Van der Loo et al, U.S. Pat. No. 3,994,818 disclose detergent compositions comprising:
(a) a $C_8$ to $C_{18}$ alcohol ethoxylate which contains from 2 to 4 moles of ethylene oxide per mole of alcohol,
(b) a $C_7$ to $C_{13}$ alcohol or mixture thereof,
(c) a $C_1$ to $C_8$ alcohol or $C_8$ to $C_{18}$ alcohol ethoxylate containing from 5 to 9 moles of ethylene oxide per mole of alcohol.

As a defoamer, a polyalkylsiloxane such as polydimethylsiloxane is added. The present invention is not concerned with the use of polysiloxanes, but rather is concerned with the use of silyl groups as capping agents to enhance the chlorine stability of nonionic surface active agents. Accordingly, the present invention differs from Van der Loo et al.

Kinstedt, U.S. Pat. No. 4,005,025 discloses aqueous anionic detergent compositions and containing an organosilane which imparts soil release benefits to hard surfaces washed therewith. The silicone compound of Kinstedt is an organic salt containing quaternary ammonium sulfur or phosphorus moieties. There is no mention of the stable silyl group capped polyethers as surfactants in the liquid cleaning detergents and no understanding of the chlorine bleach stable properties of the silyl capped polyethers of the present invention.

SUMMARY OF THE INVENTION

In accordance with the present invention, the applicants have discovered that capping nonionic copolymers of ethylene oxide and propylene oxide with alkyl, oxyalkyl and/or aryl silyl groups provides enhanced stability of the polyether polyol in cleaning compositions which include alkaline hypochlorite bleaching agents, thereby allowing these formulations to retain their cleaning and defoaming properties for longer periods of time than formulations containing conventional nonionic polyether polyol surfactants.

Conventional nonionic polyether surfactants are disclosed which are capped with alkyl, oxyalkyl and/or aryl silyl groups. The preferred surfactants, before being capped, are those having an average molecular weight range of from about 500 to 25,000 and a relatively low hydrophilic content. The hydrophilic content of the surfactant is from about 5 to 35 weight percent and the total molecular weight of the hydrophobe is from 65 to 95 weight percent of the total molecular weight of the polyether. The polyether surfactants may be block or heteric copolymers of alkylene oxides, or they may contain blocks of heteric copolymers of alkylene oxides. Suitable polyethers may be mono- through octafunctional and are capped with alkyl, oxyalkyl and/or aryl silyl groups to provide the nonionic polyether surfactants which exhibit excellent chlorine bleach stability.

These polyether surfactants may be produced in the manner conventional polyethers are produced using base catalysis and then capped with alkyl, oxyalkyl and/or aryl silyl groups at elevated temperatures over a prolonged period of time. The catalyzed polyethers are then neutralized with an acid. Other forms of catalyst removal such as ion exchange or adsorbent treatment are also anticipated.

The polyether products produced according to the present invention are polyoxyalkylene polyethers capped at each reactive hydrogen with alkyl, oxyalkyl and/or aryl silyl groups, and have a general structure which is believed to be a mixture of compounds of the formula:

$$Y[(A_1O)_n(A_2O)_m(A_3O)_p(X)_qA_4]_z$$

wherein Y is the residue of an organic compound having from 1 to 8, preferably 1 to 4, reactive hydrogens as measured by the Zerevitinov determination method; z is a number from 1 to 8, $A_1$, $A_2$ and $A_3$ are $C_2$ to $C_4$ alkylene groups, tetramethylene, and mixtures thereof; n+m+p are numbers such that the total molecular weight of the uncapped portion of the molecule is from about 500 to 25,000, X is a hydrocarbon residue containing 2 to 30 carbon atoms, preferably the residue ($-CR_1R_2CR_3R_4CR_5R_6-$) where $R_1$, $R_2$, $R_3$, $R_4$, $R_5$ and $R_6$ are H, methyl, and mixtures thereof, q is a number from 0 to 1, $A_4$ is an Si $R'_3$ group wherein $R'$ is a $C_1$ to $C_{30}$ alkyl, a $C_1$ to $C_{30}$ oxyalkyl, a $C_6$ to $C_{30}$ aryl group, and mixtures thereof.

In the above formula, $A_1O$ and $A_2O$ are preferably ethylene oxide, propylene oxide and mixtures thereof, and $A_3O$ is preferably isobutylene oxide. In addition, it is preferred that n+m+p are numbers such that the molecular weight of the hydrophile in 5 to 35 weight percent of the total molecular weight and the total molecular weight of the hydrophobe is from 65 to 95 weight percent of the total molecular weight.

The initiator Y is more preferably selected from the group consisting of methanol, ethanol, propanol, isopropanol, butanol, isobutanol, $C_5$ to $C_{18}$ branched or straight chain alcohols, $C_6$ to $C_{18}$ aryl or alkylaryl alcohols, ethylene glycol, propylene glycol, diethylene glycol, dipropylene glycol, glycerol, trimethylolpropane, pentaerythritol, ethylenediamine, diethylene tetramine, triethylenepentamine, glucose and alkyl glucosides, sucrose, alkylglucosides, and mixtures thereof.

$A_4$ is preferably trimethylsilyl, diphenyl methylsilyl, t-butyldiphenylsilyl, t-butyldimethylsilyl, and mixtures thereof.

DETAILED DESCRIPTION OF THE PREFERRED EMBODIMENT

Novel nonionic polyether surfactants have been developed which exhibit surprising stability in the presence of chlorine bleach based upon capping the polyether surfactants with alkyl, oxyalkyl and/or aryl silyl groups. In addition to their enhanced chlorine bleach stability, these surfactants are low foaming and liquid detergent compositions containing these surfactants have improved spotting and filming properties comparable to powdered detergent formulations.

The surfactants to be capped are preferably polyoxyalkylene polyethers terminated with oxyethylene groups. These terminal groups are further capped with alkyl, oxyalkyl and/or aryl silyl groups to provide the desired stability and other properties in cleaning compositions containing chlorine bleach. Generally, the terminal atom on the chains of such compounds is a hydrogen atom which is preceded by the polyoxyethylene group. However, for simplicity's sake, and as generally used in the art, the expression "terminated with the oxyethylene group," as used throughout the instant specification and claims, includes compounds having terminal hydrogen atoms.

A preferred type of oxyethylene group terminated polyoxyalkylene polyether is a cogeneric mixture of conjugated polyoxyalkylene compounds containing in their structure, oxyethylene groups, oxypropylene groups and the residue of an active hydrogen containing compound. The term "cogeneric mixture" used herein is a term that has been coined to designate a series of closely related homologues that are obtained by condensing a plurality of alkylene oxide units with a reactive hydrogen compound. This expression is well known to those skilled in the art as can be seen from U.S. Pat. Nos. 2,677,700; 2,674,619; and 2,979,528.

The active hydrogen containing compound also referred to herein as an initiator has about 1 to 30 carbon atoms, preferably about 1 to 14 carbon atoms, and at least 1, preferably about 1 to 8, active hydrogen atoms. Typical initiators useful in the present invention include monofunctional or polyfunctional alcohols such as methanol, ethanol or higher branched or unbranched monofunctional alcohols, hexyl alcohol, octyl alcohol, decyl alcohol, stearyl alcohol, and mixtures thereof, phenol, alkyl phenols and dialkyl phenols, difunctional alcohols such as ethylene glycol, propylene glycol, butylene glycol, ethylenediamine, triethylenediamine, hexylmethylenediamine, trimethylol propane, pentaerythritol, sucrose and erythritol, $C_1$-$C_{30}$ mono- or polyalkyl phenols, polyhydroxy alkylated phenols, hydrogenated (polyphenol) alkanes, polyphenols where the aromatic rings are fused or bridged by alkyl groups or are linked directly but not fused, such as diphenols, oxyalkylated alkyl amines, aniline or other aromatic amines or polyamines, fatty acids, fatty amides, oxyalkylated fatty acids, oxyalkylated fatty amides and mixtures thereof.

Broadly defined, the initiator may be a 1,2- or 1,X-difunctional alcohol where X is an integer not exceeding the number of carbon atoms in the alcohol, monoalkyl ethers of the above-mentioned glycols, or other higher functional alcohols.

Other typical initiators may include amines, amides, mercaptans and carboxylic acids. Indeed, other surfactants may be useful as starting materials for the instant invention. These include oxyalkylated amines, oxyalkylated fatty acids and oxyalkylated fatty amides.

These initiator compounds may be heteric or block, as long as they are terminated with oxyethylene groups and are characterized in that the oxyalkylene groups are attached to the initiator compound at the site of the reactive hydrogen atoms.

In one preferred embodiment of this invention, the oxyalkylene compounds are those of the type disclosed in U.S. Pat. No. 2,674,619 prepared by first oxypropylating an initiator and subsequently oxyethylating the resulting compound as more completely described in the above-mentioned patent, incorporated herein by reference. In such compounds, the polyoxypropylene groups are attached to the initiator nucleus at the site of the reactive hydrogen atoms, thereby constituting a polyoxypropylene polymer. The oxyethylene chains are attached to the polyoxypropylene polymer in oxyethylene chains. The oxypropylene chains optionally, but advantageously, contain small amounts of ethylene oxide and the oxyethylene chains optionally but advantageously contain small amounts of other alkylene oxides such as propylene oxide and/or butylene oxide. Such compounds are believed to correspond to the formula:

$$Y[(C_3H_6O)_n(C_2H_4O)_mH]_x \qquad \text{I}$$

Wherein Y is the residue of an organic compound having from about 1 to 30, preferably about 1 to 14 carbon atoms and containing x reactive hydrogen atoms in which x has a value of at least 1, preferably about 1 to 8, n has a value such that the molecular weight of the polyoxypropylene hydrophobic base is about 300 to 23,750 and m has a value such that the oxyethylene content of the molecule is from about 5 to 40, preferably 10 to 30 weight percent of the molecule or oxyalkyl moiety.

It is further noted that when the molecular weight is stated in this specification or in the claims, unless otherwise noted, there is meant the average theoretical molecular weight which equals the total of the grams of the alkylene oxide employed per mole of reactive hydrogen compound. It is well recognized in the field of alkylene oxide chemistry that the polyoxyalkylene compositions one obtains by condensing an alkylene oxide with a reactive hydrogen compound are actually polymeric mixtures of compounds rather than a single molecular compound. The mixture contains closely related homologues wherein the statistical average number of oxyalkylene groups equals the number of moles of the alkylene oxide employed and the individual members in the mixtures contain varying numbers of oxyalkylene groups. Accordingly, as already noted, the oxypropylene chains optionally but advantageously may contain small amounts of ethylene oxide and the oxyethylene chains optionally but advantageously contain small amounts of alkylene oxides such as propylene oxide and butylene oxide. Thus, the compositions of this invention are mixtures of compounds which are defined by molecular weight of the polyoxypropylene chains and weight percent of oxyethylene groups.

Preferred compounds of the Formula I are those where Y is a residue of propylene glycol, or propylene glycol mono methylether whereby the formulae then become $$CH_3-O(C_3H_6O)_n-(C_2H_4O)_mH \qquad \text{II}$$

or $$HO(C_2H_4O)_m(C_3H_6O)_n(C_2H_4O)_mH \qquad \text{IIa}$$

wherein n has a value such that the molecular weight and the polyoxypropylene hydrophobic base is about 300 to 23,750, preferably 450 to 17,500, m has a value such that the oxyethylene content of the molecule is from about 5 to 40, preferably 10 to 30 weight percent of the molecule.

Nitrogen-containing polyoxyalkylene compositions are included in the present invention which are similar to those described in U.S. Pat. No. 2,979,528. These compounds are prepared in much the same manner as those disclosed in accordance with the procedure disclosed in U.S. Pat. No. 2,679,619. However, instead of propylene glycol or propylene glycol monomethyl ether as an initiator, a reactive hydrogen compound containing nitrogen is utilized. Initiators for these compounds include ammonia, primary amines, alkylene polyamines, alkanol amine and heterocyclic nitrogen compounds. Aliphatic primary diamines, having not over 8 carbon atoms are the preferred nitrogen-containing reactive hydrogen compounds and include ethylenediamine, diethylene triamine, triethylene tetramine tetraethylene pentamine, hexamethylene diamine, phenylene diamine and the like.

Useful nitrogen-containing nonionic surfactants are mixtures of cogeneric polyoxypropylene polyoxyethylene compounds based on a nitrogen-containing reactive hydrogen compound wherein chains of oxypropylene groups having a defined molecular weight are attached to the nucleus of the reactive hydrogen compound at the sites of the hydrogen atoms and wherein the chains of oxyethylene groups are attached to opposite ends of the oxypropylene chains. The compositions are prepared by condensing propylene oxide with a nitrogen-containing reactive hydrogen compound, preferably ethylenediamine and subsequently condensing ethylene oxide with the propylene oxide-reactive hydrogen compound. The collective molecular weight of the oxypropylene chains attached to the nitrogen-containing reactive hydrogen compound must be at least about 300 and can range up to about 23,750 or higher. Where ethylenediamine is the reactive hydrogen compound, these compounds are believed to have the following formula:

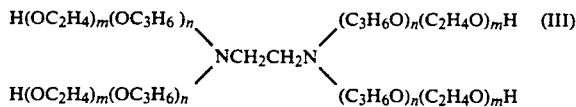

wherein n has a value such that the overall molecular weight of the polyoxypropylene hydrophobic base is about 300 to 23,750, preferably about 450 to 17,500, and m has a value such that the polyoxyethylene hydrophilic base is from about 5 to 35, weight percent of the molecule. Amine oxides of structure III are also anticipated to be of utility.

Other preferred polyether surfactants are those wherein Y in Formula I above is methanol.

The instant invention is also applicable to conventional oxypropylene group terminated polyoxyalkylene polyols. More specifically, polymers prepared by reacting all the hydroxyl groups of the oxyethylene group terminated polyols with propylene oxide. For example, the polyols to be capped with the oxypropylene groups prior to capping with alkyl, oxyalkyl and/or aryl silyl groups could be polyoxyethylene polyethers similar to those described above, but having oxypropylene terminal groups such as those disclosed, including preparation thereof, in U.S. Pat. No. 3,036,118; which is oxypropylene group terminated. When such compounds are capped with oxypropylene groups by conventional means, a product may be produced which also presents chlorine bleach stability problems, which may be met by capping the surfactant so formed with alkyl, oxyalkyl and/or aryl silyl ethers. Similarly, heteric polyoxyalkylene polyethers such as polyethers incorporating a heteric mixture of oxypropylene and oxyethylene groups when capped with oxypropylene rich groups by methods known to those skilled in the art present the same problems with regard to chlorine bleach stability. These problems are addressed by capping the surfactants with alkyl, oxyalkyl and/or aryl silyl groups, as will hereinafter be described.

Such polyoxyalkylene polyols capped with oxypropylene groups are believed to have the following generalized formula:

$$Y[(A)_m(C_3H_6O)_nH]_x \qquad \text{IV}$$

wherein A is an oxyalkylene hydrophilic group selected from oxyethylene, which may contain small amounts of oxypropylene, oxybutylene, oxytetramethylene, as a heteric block thereof; m and n are whole numbers selected to give an overall molecular weight of the product of about 500 to 25,000; Y is as set forth above and n represents a value whereby the total number of oxypropylene groups in the compound is about 5 to 410.

In a preferred embodiment, x is 1 to 8, A comprises oxyethylene groups centrally located in the molecule with oxypropylene groups attached at each end thereof. In another embodiment, A is a heteric mixture of oxypropylene or oxybutylene groups with the oxyethylene groups. The preferred compounds prior to capping with oxypropylene generally have the formula:

$$Y[(C_2H_4O)_m(C_3H_6O)_nH]]_x \qquad \text{V}$$

wherein Y is the residue of an organic compound having about 1 to 14 carbon atoms; x is the number of reactive hydrogen atoms and is from about 1 to 8; n has a value such that the molecular weight of all the polyoxypropylene in the conventional surfactant is from about 300 to 23,750 and m has a value such that the oxyethylene content of the molecule is from about 5 to 40, preferably 10 to 30 weight percent of the molecule. A preferred compound of this type prior to capping with oxypropylene is one wherein Y is ethylene glycol or propylene glycol whereby the formula is:

$$HO[(C_2H_4O)_m(C_3H_6O)_n]H \qquad \text{VI}$$

wherein m has the value set forth above for Formula V and n has a value such that the total molecular weight of the polyoxypropylene hydrophobic base is from about 300 to 23,750. These compounds are more particularly described in U.S. Pat. No. 3,036,118 incorporated herein by reference. In the products which are of the type more particularly described in U.S. Pat. No. 2,979,528, except that the propylene oxide and ethylene oxide groups are in reverse order, Y can also represent the reactive hydrogen compounds containing nitrogen and having up to about 6, inclusive, carbon atoms. A preferred compound of this type is one where Y is ethylenediamine and the formula is:

$$\begin{array}{c} H(OC_3H_6)_n(OC_2H_4)_m \\ \diagdown \\ \diagup \\ H(OC_3H_6)_n(OC_2H_4)_m \end{array} NCH_2CH_2N \begin{array}{c} (C_2H_4O)_m(C_3H_6O)_nH \\ \diagup \\ \diagdown \\ (C_2H_4O)_m(C_3H_6O)_nH \end{array} \qquad \text{VII}$$

wherein n has a value such that the molecular weight of all the polyoxypropylene hydrophobic groups is about 300 to 23,750 and m has a value such that the oxyethylene content of the molecule is from about 5 to 35 weight percent of the molecule. Heteric structures are also included and the formula is modified accordingly as is well known to one skilled in the art. Amine oxides of such surfactants are anticipated as being of utility.

In another embodiment, Y in Formulas IV and V is trimethylolpropane.

The polyethers of Formulas V, VI, and VII are then capped with oxypropylene groups prior to their being capped with alkyl, oxyalkyl and/or aryl silyl groups, by methods well known to those skilled in the art whereby the total number of oxypropylene groups in the compound is from about 5 to 410.

The polyether surfactants described above are then capped with alkyl, oxyalkyl and/or aryl silyl groups at the sites of the terminal hydrogen or hydroxyl groups. The alkyl, oxyalkyl and/or aryl silyl groups are of the general formula:

$$Si-R^1{}_3$$

wherein $R^1$ is a $C_1$ to $C_{30}$ alkyl, $C_1$ to $C_{30}$ oxyalkyl, a $C_6$ to $C_{30}$ aryl group, and mixtures thereof.

Those silyl groups of particular interest may be selected from the group consisting of trimethylsilyl, diphenylmethylsilyl, t-butyldiphenylsilyl, t-butyldimethylsilyl and mixtures thereof.

These alkyl oxyalkyl and/or aryl silyl groups are added to the polyether surfactants in the presence of alkylene oxide addition catalysts such as are well known to those skilled in the art. The resulting capped polyether surfactants have the formula $$Y[(A_1O)_n(A_2O)_m(A_3O)_p(X)_qA_4]_z$$

wherein Y is the residue of an organic compound having from 1 to 8, preferably 1 to 4, reactive hydrogens as measured by the Zerevitinov determination method; z is a number from 1 to 8, $A_1$, $A_2$ and $A_3$ are $C_2$ to $C_4$ alkylene groups, tetramethylene, and mixtures thereof; n+m+p are numbers such that the total molecular weight of the uncapped portion of the molecule is from about 500 to 25,000, X is a hydrocarbon residue containing 2 to 30 carbon atoms, preferably the residue ($-CR_1R_2CR_3R_4$ $CR_5R_6-$) where $R_1$, $R_2$, $R_3$, $R_4$, $R_5$ and $R_6$ are H, methyl, and mixtures thereof, q is a number from 0 to 1, $A_4$ is an Si $R'_3$ group wherein $R'$ is a $C_1$ to $C_{30}$ alkyl, a $C_1$ to $C_{30}$ oxyalkyl, a $C_6$ to $C_{30}$ aryl group, and mixtures thereof.

In the above formula, $A_1O$ and $A_2O$ are preferably ethylene oxide, propylene oxide and mixtures thereof, and $A_3O$ is preferably isobutylene oxide. In addition, it is preferred that n+m+p are numbers such that the molecular weight of the hydrophile in 5 to 35 weight percent of the total molecular weight and the total molecular weight of the hydrophobe is from 65 to 95 weight percent of the total molecular weight of the polyether.

The initiator Y is more preferably selected from the group consisting of methanol, ethanol, propanol, isopropanol, butanol, isobutanol, $C_5$ to $C_{18}$ branched or straight chain alcohols, $C_6$ to $C_{18}$ aryl or alkylaryl alcohols, ethylene glycol, propylene glycol, diethylene glycol, dipropylene glycol, glycerol, trimethylolpropane, pentaerythritol, ethylenediamine, diethylene tetramine, triethylenepentamine, glucose and alkyl glucosides, sucrose, alkylglycosides, and mixtures thereof.

$A_4$ is preferably trimethylsilyl, diphenylmethyl silyl, t-butyldiphenyl silyl, t-butyldimethyl silyl, and mixtures thereof.

The chlorine bleach stable surfactants of the present invention are most useful when formulated in cleaning products containing chlorine bleach such as products for home dishwashing, wearwashing, hard surface and metal cleaning or other uses. In such products, the chlorine bleach attacks conventional nonionic surfactants and reduces their spotting and defoaming properties. Such attack also reduces the chlorine bleach content of such products. By use of the present invention, nonionic surfactants may be incorporated into detergent compositions which allow for longer shelf life than products currently in use.

Useful cleaning compositions incorporating the chlorine bleach stable polyoxyalkylene polyethers of the instant invention generally include additional components which make up the formulated detergent composition.

The manner of using these components by incorporating in a dishwashing, laundry, hard surface cleaner, or other detergent composition is well known to those skilled in the art. Such additional components include other surfactants, chlorine releasing agents, builders, and additives such as bleaches, abrasives, fillers, dyes, perfumes, soil anti-redeposition agents, corrosion inhibitors, silicates, alkalies, processing aids, hydrotropes, etc.

The preferred nonionic surfactants employed as additional components include the oxyethylene group terminated compounds of Formulas I, II, IIa, and III, set forth above. Other nonionics that may be employed include the polyoxyethylene-polyoxypropylene condensates of alkylphenols having from about 6 to 20 carbon atoms in the alkyl portion and from about 5 to 30 ethyleneoxy groups and/or propyleneoxy in the polyoxyalkylene radical, alkylene oxide adducts of higher aliphatic alcohols and thioalcohols having from about 8 to 22 carbon atoms in the aliphatic portion and about 3 to 50 oxyalkylene units in the oxyalkylene portion and which are preferably oxyethylene group terminated. Other well known nonionics may also be employed.

Important components of cleaning compositions, particularly automatic dishwashing detergents, are the builders or builder salts such as alkaline condensed phosphate salts, for instance, tetrasodium pyrophosphate and those polyphosphates of the calcium and magnesium ion sequestering type whose $Na_2O/P_2O_5$ ratios range from 1:1 to 1.67:1 and 20 to 80 weight percent of an alkaline detergent salt such as sodium carbonate, sodium bicarbonate and mixtures thereof, di- and trisodium orthophosphate, sodium metasilicate, sodium sesquisilicate, borax and sodium borate, sodium hydroxide and potassium hydroxide.

Alternatively to the use of phosphate builders, any of the water-soluble metal salts of citric acid can be used in the practice of the present invention. However, all salts do not serve with equal effectiveness, and the alkali metal salts, particularly the sodium and potassium citrates, are preferred. Suitable proportions of silicates in dishwashing formulations are employed to overcome certain difficulties. The silicate used is preferably solid granular sodium metasilicate, a commercially available material. Sodium silicates in which the mole ratio of $SiO_2:Na_2O$ are more than 1:1, e.g., 2:1 or 3:1, may be used in place of the sodium metasilicate.

The combination of the citrate and condensed phosphate salt (e.g., sodium tripolyphosphate) appears to result in an enhanced activity.

Active chlorine-containing compounds or chlorine-releasing compounds are often desirable in cleaning compositions. Such compounds which may be employed in accordance with the instant invention include chlorinated trisodium phosphate, trichlorocyanuric acid, sodium salt of dichlorocyanuric acid, potassium salt of dichlorocyanuric acid, sodium hypochlorite, potassium hypochlorite, and 1,3-dichloro-5,5-dimethylhydantoin.

Suitable hydrotropes that may be employed include sodium xylene sulfonate, sodium-2-ethylhexyl sulfates, amine alkylaryl sulfonates, alkyl napthalene sulfonates, dodecyl benzene sulfonates and sodium dialkyl sulfosuccinates.

The term "additives" as defined herein and used throughout this specification and claims does not include other surfactants, builder salts and chlorine releasing compounds which are referred to separately.

Preferred cleaning compositions employing products of this invention will comprise from about 0.1 to 5 percent, preferably about 1 to 4 percent polyoxyalkylene polyether surfactant capped with alkyl, oxyalkyl and/or aryl silyl groups, and about 95 to 99 percent, preferably about 96 to 99 percent of machine dishwashing components selected from the group consisting of other surfactants, builder salts, chlorine releasing agents, additives and mixtures thereof. A suitable cleaning composition may contain from about 0.1 to 5 percent, preferably about 1 to 4 percent of the polyoxyalkylene polyether surfactant capped with an alkyl, oxyalkyl and/or aryl silyl group, about 0.1 to 5 percent, conventional surfactants, about 0.1 to 5 percent, preferably about 0.9 to 1.5 percent available chlorine, about 25 to 80 percent, preferably about 35 to 60 percent builder salts, and about 0 to 60 percent, preferably about 5 to 40 percent additives, and the balance water. Since different chlorine releasing compounds have differing percentages of available chlorine, the amount is expressed herein as percent available chlorine.

When used for washing purposes such as in a dishwashing application, such solution may contain about 0.1 to 0.5, and preferably about 0.15 to 0.3 percent of the total detergent composition set forth above, balance water.

When used as a hard surface cleaner, or as a detergent, the composition may contain, in addition to the above, 1 to 65 percent alkaline source, solvents and other additives.

The following Examples are offered to illustrate various aspects of the invention. Those skilled in the art appreciate that many variations are possible, and the examples are not to be construed as limiting the scope and spirit of the invention.

In the Examples, the amount of available chlorine in the formulation was determined using conventional iodometric titration techniques, with adjustments to accommodate the bases used, as are well known to those skilled in the art.

EVALUATION OF CHLORINE STABILITY

A mixture of 1 weight percent surfactant, 1 weight percent NaOH, and sufficient industrial grade NaOCl bleach to obtain 2 percent available chlorine and distilled water were blended in 4 ounce French Square bottles equipped with a TEFLON ® fluorinated hydrocarbon coated stirring bar. The material was stirred while blending. They were then placed in a 100° F. oven, and analyzed for available chlorine at 7 to 14 day intervals. Samples were stirred prior to analyzing for available chlorine. The remaining available chlorine in the samples was determined by wet analysis using standard iodometric titration techniques.

SYNTHESIS OF SILYL-ETHER-CAPPED POLYETHERS

For examples 3,4,5 and 6 in Table 1, the same basic synthetic route was used. The synthesis of the compound given as Example 6 in Table 1 is shown below.

Tert-Butyldimethylsilyl Capping of Isobutyleneoxidemodified polyoxyethylene/polyoxypropylene polyol.

A. Base Surfactant Synthesis

The reactor was a stainless-steel one-gallon, Autocalve Engineers autoclave with 150 psig working pressure limit. It was charged with 2476 g (1.33 moles, 2.5 equivalents) of the surfactant described as Example 1 in Table 1. 25 g (0.25 moles, 0.1 equivalents) of potassium-tert-butoxide (Aldrich, 97%) was added. The reactor was sealed, and evacuated for one hour at 100° C. The reactor was then cooled to room temperature. 197 g (2.7 moles) of isobutylene oxide were added. The reactor was then heated to 100° C. for three hours and 45 minutes. The product was cooled and discharged, and used for subsequent syntheses. This product had a hydroxyl content of 5.5 mg KOH/g sample.

B. Silylation 100.71 g (0.05 mol, 0.0936 OH equivalents) of the surfactant synthesised as in A) above were added to a 250 ml, 3-necked flask equipped with a mechanical stirrer and vacuum adaptor, the third neck being stoppered. The flask was evacuated slowly with stirring, and after 15 minutes of full vacuum, a heating mantle was placed under the flask and turned on. The surfactant was stripped at 100° C. for one hour under full vacuum. The vacuum was sealed off, and nitrogen was allowed to enter the flask. 2.18 g (0.088 mol) of NaH (97%, Aldrich) were weighed out into a small vial, which was then connected to the third neck of the reaction flask via a large rubber hose, under fast flow of nitrogen. The NaH was added slowly to the reaction flask over a period of about 4 hours so as to reduce foaming. The remainder of the NaH added was an approximately 50 percent slurry in mineral oil, 0.64 g (0.013 mol) were added. A total of 10 percent (Equivalent) excess of hydride was added. After all NaH was added, the reaction was allowed to stir at 100° C. for an additional period of about 6 hours, and then allowed to cool. Then 15.44 g (0.093 mol) of tert-butyldimethylsilyl chloride (PCR Inc., Gainesville, Fl) were added to the reaction flask under fast flow of nitrogen. The mixture was heated to 100° C. for 6 hours, and then allowed to cool and stir over the weekend at room temperature. The white precipitate was filtered out with difficulty through celite, using a fine filter frit. The recovered yield was not determined.

The infrared spectrum indicated an OH stretch band intensity at 3470 cm$^{-1}$ of 0.013 absorbance units, compared to 0.116 for the starting material, indicating 89 percent chemical yield. This is approximate, as two salt plates were used. However, several peaks in other regions were almost the same height, indicating similar thickness of the film between the plates in both spectra.

TABLE I

Half Life of Active Chlorine in Detergents Prepared With Alkyl/Aryl Silyl-Capped Versus Base Surfactant

| Example Number | Base Surfactant | Surfactant Cap | % Capping | Half Life Weeks |
|---|---|---|---|---|
| 1 | EOxPOyEOx' ~1900, 13 Wt % EO | None | 0 | 5 |
| 2 | EOxPOyEOx' ~1900, 13 Wt % EO | Isobutylene oxide | 85 | 7 |
| 3 | EOxPOyEOx' ~1900, 13 Wt % EO | IBO + Trimethyl silyl | 100 | 10 |
| 4 | EOxPOyEOx' ~1900, 13 Wt % EO | IBO + diphenyl methylsilyl | 61 | 8 |
| 5 | EOxPOyEOx' ~1900, 13 Wt % EO | IBO + t-butyl, diphenylsilyl | 87 | 8 |
| 6 | EOxPOyEOx' ~1900, 13 Wt % EO | IBO + t-butyl, dimethyl silyl | 89 | 8 |

There is a significant increase in chlorine bleach stability of the capped nonionic surfactant over the uncapped surfactant, with best results seen in Example 3.

The embodiments of the invention in which an exclusive privilege or property is claimed are defined as follows:

1. A liquid chlorine bleach stable polyether surfactant having the general formula:

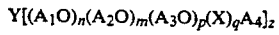

wherein Y is the residue of an organic compound having from 1 to 8, reactive hydrogens as measured by the Zerevitinov determination method; z is a number from 1 to 8, $A_1$, $A_2$ and $A_3$ are $C_2$ to $C_4$ alkylene groups, tetramethylene, and mixtures thereof; n+m+p are numbers such that the total molecular weight of the uncapped portion of the molecule is from about 500 to 25,000, said uncapped portion of the molecule having hydrophilic and hydrophilic moieties such that the molecular weight of the hydrophile is from 5 to 35 weight percent of the total molecular weight and the total molecular weight of the hydrophobe is from 65 to 95 weight percent of the total molecular weight; and X is a hydrocarbon residue containing 2 to 30 carbon atoms q is a number from 0 to 1, $A_4$ is a Si $R'_3$ group wherein $R'$ is a $C_1$ to $C_{30}$ alkyl, a $C_1$ to $C_{30}$ oxyalkyl, a $C_6$ to $C_{30}$ aryl group, and mixtures thereof.

2. The polyether of claim 1, wherein $A_3O$ is isobutylene oxide.

3. The polyether of claim 1, wherein $A_4$ is a silyl group selected from the group consisting of trimethylsilyl, diphenylsilyl, t-butyldiphenylsilyl, t-butyldimethylsilyl, and mixtures thereof.

4. The polyether of claim 1, wherein Y is selected from the group consisting of methanol, ethanol, $C_3$-$C_{30}$ alkanols, ethylene glycol, propylene glycol, butylene glycol, higher 1,2- or 1, X-difunctional alcohols where X is an integer not exceeding the number of carbons in the alcohol, mono-alkyl ethers of the above mentioned glycols, glycerine, ethylenediamine, a polyamine, triethylenediamine, hexamethylene diamine, trimethylolpropane, erythritol, pentaerythritol, sucrose, nonylphenol, octyl phenol, phenol or $C_1$-$C_{30}$ mono- or polyalkyl phenols, polyhydroxy alkylated phenols, hydrogenated (polyphenol) alkanes, polyphenols where the aromatic rings are fused or bridged by alkyl groups or are linked directly but not fused, such as diphenols, oxyalkylated alkyl amines, aniline, aromatic amines, polyamines, fatty acids, fatty amides, oxyalkylated fatty acids, oxyalkylated fatty amides and mixtures thereof.

5. The polyether of claim 1, wherein $A_1O$ and $A_2O$ are ethylene oxide, propylene oxide, and mixtures thereof.

6. A liquid automatic dishwashing detergent composition having improved chlorine bleach stability comprising:
(a) an active chlorine containing compound selected from the group consisting of chlorinated trisodium phosphate, chlorinated cyanuric acid and alkali metal salts thereof, 2,3-dichloro-5, 5-dimethyldantoin, hypochlorite bleach and mixtures thereof to yield available chlorine in an amount of from about 0.1 percent to 5 percent;
(b) about 0.1 percent to 5 percent of a chlorine bleach stable nonionic surfactant having the general formula:

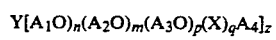

wherein Y is the residue of an organic compound having from 1 to 8 reactive hydrogens as measured by the Zerevitinov determination method; z is a number from 1 to 8, $A_1$, $A_2$ and $A_3$ are $C_2$ to $C_4$ alkylene groups, tetramethylene, and mixtures thereof; n+m+p are numbers such that the total molecular weight of the uncapped portion of the molecule is from about 500 to 25,000, said uncapped portion of the molecule having hydrophilic moieties such that the molecular weight of the hydrophile is 5 to 35 weight percent of the total molecular weight and the total molecular weight of the hydrophobe is from 65 to 95 weight percent of the total molecular weight, X is a hydrocarbon residue containing 2 to 30 carbon atoms, q is a number from 0 to 1, $A_4$ is a Si-$R'_3$ group wherein $R'$ is a $C_1$ to $C_{30}$ alkyl, a $C_1$ to $C_{30}$ oxyalkyl, a $C_6$ to $C_{30}$ aryl group, and mixtures thereof; and (c) the balance water.

7. The detergent composition of claim 6, wherein $A_3O$ is isobutylene oxide.

8. The detergent composition of claim 6, wherein $A_4$ is a silyl group selected from the group consisting of trimethylsilyl, diphenylsilyl, t-butyldiphenylsilyl, t-butyldimethylsilyl, and mixtures thereof.

9. The detergent composition of claim 6, wherein Y is selected from the group consisting of methanol, ethanol, $C_3$-$C_{30}$ alkanols, ethylene glycol, propylene glycol, butylene glycol, higher 1,2- or 1, X-difunctional alcohols where X is an integer not exceeding the number of carbons in the alcohol, mono-alkyl ethers of the above mentioned glycols, glycerine, ethylenediamine, a polyamine, triethylenediamine, hexamethylene diamine, trimethylolpropane, erythritol, pentaerythritol, surcrose, nonylphenol, octyl phenol, phenol or $C_1$-$C_{30}$ mono- or polyalkyl phenols, polyhydroxy alkylated phenols, hydrogenated (polyphenol) alkanes, polyphenols where the aromatic rings are fused or bridged by alkyl groups or are linked directly but not fused, such as diphenols, oxyalkylated alkyl amines, aniline, aromatic amines, polyamines, fatty acids, fatty amides, oxyalkylated fatty acids, oxyalkylated fatty amides and mixtures thereof.

10. The detergent composition of claim 6, wherein $A_1O$ and $A_2O$ are ethylene oxide, propylene oxide, and mixtures thereof.

11. The detergent composition of claim 6, further including about 1 to 20 percent by weight water, about 1 to 10 percent by weight filler, and an alkaline condensed phosphate salt.

12. The detergent composition of claim 6, further including:
(a) about 20 to about 80 percent by weight of an alkaline detergent salt selected from at least one of the group consisting of sodium hydroxide, potassium hydroxide, sodium carbonate, sodium bicarbonate, disodium orthophosphate, trisodium orthophosphate, sodium metasilicate, sodium sesquisilicate, sodium sulfate and sodium bisulfate;
(b) about 20 to about 80 percent by weight of (1) a water-soluble metallic salt of citric acid or an organic sequestering agent selected from the group consisting of at least one of tetrasodium ethylene diamine tetraacetate and a water-soluble metal salt of nitrilotriacetic acid or (2) alternatively, an alkaline condensed phosphate salt selected from the group consisting of at least one of tetrasodium pyrophosphate, sodium tripolyphosphate, and those polyphosphates of the calcium and magnesium ion sequestering type having $Na_2O/P_2O_5$ weight ratios ranging from 1:1 to 1.67:1, or (3) mixtures of (1) and (2).

13. A liquid hard surface cleaner composition having improved chlorine bleach stability, comprising:
(a) an active chlorine containing compound selected from the group consisting of chlorinated trisodium phosphate, chlorinated cyanuric acid and alkali metal salts thereof, 2,3-dichloro-5,5-dimethylhydantoin, hypochlorite bleach and mixtures thereof to yield chlorine in an amount of from about 0.1 to 5 percent;
(b) about 0.1 to 5 percent of a chlorine bleach stable nonionic surfactant having the general formula:

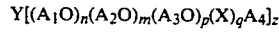

wherein Y is the residue of an organic compound having from 1 to 8 reactive hydrogens as measured by the Zerevitinov determination method; z is a number from 1 to 8, $A_1$, $A_2$ and $A_3$ are $C_2$ to $C_4$ alkylene groups, tetramethylene, and mixtures thereof; n+m+p are numbers such that the total molecular weight of the uncapped portion of the molecule is from about 500 to 25,000, said uncapped portion of the molecule having hydrophilic moieties such that the molecular weight of the hydrophile is 5 to 35 weight percent of the total molecular weight and the total molecular weight of the hydrophobe is from 65 to 95 weight percent of the total molecular weight, X is a hydrocarbon residue containing 2 to 30 carbon atoms q is a number from 0 to 1, $A_4$ is an Si $R'_3$ group wherein $R'$ is a $C_1$ to $C_{30}$ alkyl, a $C_1$ to $C_{30}$ oxyalkyl, a $C_6$ to $C_{30}$ aryl group, and mixtures thereof;

(c) about 0.1 through 65 weight percent alkalinity source; and (d) the balance water.

14. The detergent composition of claim 13, wherein $A_4$ is a silyl group selected from the group consisting of trimethylsilyl, diphenylsilyl, t-butyldiphenylsilyl, t-butyldimethylsilyl, and mixtures thereof.

15. The cleaning composition of claim 13, wherein Y is selected from the group consisting of methanol, ethanol, $C_3$-$C_{30}$ alkanols, ethylene glycol, propylene glycol, butylene glycol, higher 1,2- or 1, X-difunctional alcohols where X is an integer not exceeding the number of carbons in the alcohol, mono-alkyl ethers of the above mentioned glycols, glycerine, ethylenediamine, triethylenediamine, hexamethylenediamine, trimethylopropane, pentaerythritol, mono- and disaccharides, nonylphenol, octylphenol, $C_1$-$C_{30}$ mono- or polyalkyl phenols, polyhydroxy alkylated phenols, hydrogenated (polyphenol) alkanes, polyphenols where the aromatic rings are fused or bridged by alkyl groups or are linked directly but not fused, such as diphenols, oxyalkylated alkyl amines, aniline or other aromatic amines or polyamines, fatty acids, fatty amides, oxyalkylated fatty acids, oxyalkylated fatty amides and mixtures thereof, oxyalkylated alkyl amines, oxyalkylated fatty acids, oxyalkylated fatty amides and mixtures thereof.

16. The composition of claim 13, wherein $A_1O$ and $A_2O$ are ethylene oxide, propylene oxide and mixtures thereof.

17. The composition of claim 13, further including builders, solvents, hydrotropes and other additives.

18. The composition of claim 13, wherein $A_3O$ is isobutylene oxide.

19. A liquid chlorine bleach stable polyether surfactant having the general formula:

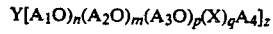

wherein Y is selected from the group consisting of methanol, ethanol, $C_3$-$C_{30}$ alkanols, ethylene glycol, propylene glycol, butylene glycol, higher 1,2- or 1, X-difunctional alcohols where X is an integer not exceeding the number of carbons in the alcohol, monoalkyl ethers of the above mentioned glycols, glycerine, trimethylolpropane, erythritol, pentaerythritol, sucrose, nonylphenol, octyl phenol, phenol or $C_1$-$C_{30}$ mono- or polyalkyl phenols, polyphenols where the aromatic rings are fused or bridged by alkyl groups or are linked directly but not fused, such as diphenols, wherein z is a number from 1 to 8, $A_1$, $A_2$ and $A_3$ are $C_2$ to $C_4$ alkylene groups, and mixtures thereof; n+m+p are numbers such that the total molecular weight of the uncapped portion of the molecule is from about 500 to 25,000, said uncapped portion of the molecule having hydrophilic moieties such that the molecular weight of the hydrophile is from 5 to 35 weight percent of the total molecular weight and the total molecular weight of the hydrophobe is from 65 to 95 weight percent of the total molecular weight; and X is a hydrocarbon residue containing 2 to 30 carbon atoms q is a number for 0 to 1, $A_4$ is a Si-$R'_3$ group wherein $R'$ is a $C_1$ to $C_{30}$ oxyalkyl, a $C_6$ to $C_{30}$ aryl group, and mixtures thereof.

* * * * *